United States Patent
Sakurai et al.

(10) Patent No.: US 10,471,171 B2
(45) Date of Patent: Nov. 12, 2019

(54) OPHTHALMIC SOLUTION

(71) Applicant: NOF CORPORATION, Tokyo (JP)

(72) Inventors: Shunsuke Sakurai, Kawasaki (JP); Koji Miyamoto, Kawasaki (JP); Yohei Takada, Kawasaki (JP); Yoshihisa Shimamura, Kawasaki (JP); Mao Maruhashi, Kawasaki (JP); Nobuyuki Sakamoto, Kawasaki (JP)

(73) Assignee: NOF Corporation, Tokyo (JP)

( * ) Notice: Subject to any disclaimer, the term of this patent is extended or adjusted under 35 U.S.C. 154(b) by 354 days.

(21) Appl. No.: 14/914,066

(22) PCT Filed: Aug. 5, 2014

(86) PCT No.: PCT/JP2014/070616
§ 371 (c)(1),
(2) Date: Feb. 24, 2016

(87) PCT Pub. No.: WO2015/029717
PCT Pub. Date: Mar. 5, 2015

(65) Prior Publication Data
US 2016/0199526 A1    Jul. 14, 2016

(30) Foreign Application Priority Data

Aug. 30, 2013 (JP) .................................. 2013-178901

(51) Int. Cl.
| | |
|---|---|
| A61K 9/00 | (2006.01) |
| A61K 31/155 | (2006.01) |
| A61K 47/02 | (2006.01) |
| A61K 47/32 | (2006.01) |
| A61K 47/38 | (2006.01) |
| A61L 12/14 | (2006.01) |
| A61L 12/10 | (2006.01) |
| A61K 47/34 | (2017.01) |

(52) U.S. Cl.
CPC ............ *A61L 12/10* (2013.01); *A61K 9/0048* (2013.01); *A61K 31/155* (2013.01); *A61K 47/02* (2013.01); *A61K 47/32* (2013.01); *A61K 47/34* (2013.01); *A61K 47/38* (2013.01); *A61L 12/14* (2013.01); *A61L 12/141* (2013.01); *A61L 12/142* (2013.01)

(58) Field of Classification Search
None
See application file for complete search history.

(56) References Cited

U.S. PATENT DOCUMENTS

| | | | |
|---|---|---|---|
| 2001/0036966 A1 | 11/2001 | Yasueda et al. | |
| 2003/0153622 A1* | 8/2003 | Hozumi | A61L 12/141 422/28 |
| 2003/0186825 A1* | 10/2003 | Mitani | A61L 12/142 510/112 |
| 2006/0035842 A1 | 2/2006 | Tsuzuki et al. | |
| 2008/0261841 A1 | 10/2008 | Heiler | |
| 2010/0197811 A1 | 8/2010 | Suzuki | |

FOREIGN PATENT DOCUMENTS

| | | | |
|---|---|---|---|
| CN | 101594779 A | 12/2009 | |
| CN | 102548562 A | 7/2012 | |
| JP | H07-166154 A | 6/1995 | |
| JP | H10-324634 A | 12/1998 | |
| JP | H11-29463 A | 2/1999 | |
| JP | 2002-258223 A | 9/2002 | |
| JP | 2003-160482 A | 6/2003 | |
| JP | 2003160482 A * | 6/2003 | ............ A61L 12/141 |
| JP | 2004-530644 A | 10/2004 | |
| JP | 2006-176501 A | 7/2006 | |
| JP | 2006-282586 A | 10/2006 | |
| JP | 2008-088174 A | 4/2008 | |
| JP | 2010-106015 A | 5/2010 | |
| WO | 2004/084877 A1 | 10/2004 | |
| WO | 2009/001899 A1 | 12/2008 | |

OTHER PUBLICATIONS

Kobayashi-Ando et al., "Reducing the cytotoxicity of polyhexamethylene biguanide (PHMB) by formulation with an MPC polymer". Journal of Japan Contact Lens Society, vol. 52, No. 4, pp. 265-269 (2010). English translation submitted of article.*
PCT International Preliminary Report on Patentability dated dated Mar. 10, 2016 in connection with PCT International Patent Application No. PCT/JP2014/070616, 13 pages.
Ryota Kobayashi-Ando et al., "Reducing the cytotoxicity of polyhexamethylene biguanide (PHMB) by formulation with an MPC polymer", Journal of Japan Contact Lens Society, vol. 52, No. 4, pp. 265-269 (2010). English Abstract.
Charles H. Powell et al., "Lipophilic versus hydrodynamic modes of uptake and release by contact lenses of active entities used in multipurpose solutions", Contact Lens Anterior Eye, vol. 33, pp. 9-18 (2010).

(Continued)

*Primary Examiner* — Gigi G Huang
(74) *Attorney, Agent, or Firm* — Amster, Rothstein & Ebenstein LLP

(57) ABSTRACT

Provided is an ophthalmic solution of which preservative component, hexamethylene biguanide, contained therein is inhibited from being adsorbed on soft contact lenses and eye droppers. The ophthalmic solution contains, at a specific ratio, (A) hydroxypropyl methylcellulose having 28.0 to 30.0 mass % methoxy groups and 7.0 to 12.0 mass % hydroxypropoxy groups, both with respect to the total amount of the hydroxypropyl methylcellulose, at a methoxy group/hydroxypropoxy group ratio of 2.5 to 4.0 by mass, wherein a 2 mass % aqueous solution of the hydroxypropyl methylcellulose at 20° C. has a viscosity of 50 to 4000 mPa·s; (B) sodium chloride or potassium chloride; (C) hexamethylene biguanide or a salt thereof; (D) 2-methacryloyloxyethyl phosphorylcholine/butyl methacrylate copolymer; and (E) water.

1 Claim, No Drawings

(56) References Cited

OTHER PUBLICATIONS

Takashi Sakimoto, "Adsorption of Preservatives on Therapeutic Soft Contact Lenses", Journal of Japan Contact Lens Society, vol. 35, pp. 177-192 (1993). English Abstract.
Written Opinion received for PCT Patent Application No. PCT/JP2014/070616 dated Nov. 4, 2014, 7 pages.
International Search Report received for PCT Patent Application No. PCT/JP2014/070616 dated Nov. 4, 2014, 4 pages.
Office Action dated May 8, 2018 in counterpart Taiwanese patent application No. 103129666.
Hydroxypropyl methylcellulose, http://www.djjxhg.com/view.asp?nid=483 (Aug. 17, 2003), http://hbpykj.com/cn/photo/qiangbingji08.html (Jul. 26, 2005).
Office Action in counterpart Chinese Application No. 201480047431.1 dated May 3, 2018.

* cited by examiner

OPHTHALMIC SOLUTION

CROSS-REFERENCE TO RELATED APPLICATIONS

This application is a U.S. national stage entry under 35 U.S.C. § 371 of PCT International Patent Application No. PCT/JP2014/070616, filed Aug. 5, 2014, which claims priority to Japanese Patent Application No. 2013-178901, filed Aug. 30, 2013, the contents of which are incorporated herein by reference into the subject application.

FIELD OF ART

The present invention relates to an ophthalmic solution in which preservative component, hexamethylene biguanide, is inhibited from being adsorbed on soft contact lenses or eye droppers.

BACKGROUND ART

Dry eye symptoms are known to be caused by reduced rate of blinking due to overuse of eyes by "watching" television, computer screen, mobile computers, or the like, or by evaporation of lacrimal fluid due to dry air created by air conditioning. It has been reported that soft contact lens wearers, compared to non-soft contact lens wearers, tend to suffer from dry eye symptoms, due to increased evaporation of lacrimal fluid from the soft contact lens surface (Non-patent Publication 1). For relief or treatment of dry eye symptoms, supplementation of lacrimal fluid with an ophthalmic solution, i.e., artificial tear preparations, is commonly employed. Almost all such ophthalmic solutions contain preservatives for ensuring the product quality during a certain circulation period (Non-patent Publication 1).

Typical preservatives contained in ophthalmic solutions are benzalkonium chloride and hexamethylene biguanide hydrochloride. Even at a content of as low as not more than 0.01% w/v (weight/volume), benzalkonium chloride and hexamethylene biguanide hydrochloride are known to be adsorbed on soft contact lenses (Non-patent Publications 2 and 3). These compounds are also reported to have adverse effects on corneal cells, and may further cause eye damages (Non-patent Publication 4). In this regard, researches have been made to reduce the adverse effects of the compounds on corneal cells (Patent Publications 1, 2, and 3).

On the other hand, the trace preservatives are also known to be adsorbed on eye droppers or the like, as disclosed in Patent Publications 4 and 5, and this may cause gradual decrease of the active preservatives in the eye dropper, to result in weakened preservative effect.

In view of the above, for avoiding contamination of the eyes with microorganisms even when the preservative effect of ophthalmic solutions is weakened, package inserts of the ophthalmic solutions provide warnings for administration and expiration date. Irrespective of this, it is reported that some patients administer an ophthalmic solution with the tip of the eye dropper nozzle in contact with their ocular surface (Non-patent Publication 5). By contacting the tip of the eye dropper nozzle with the ocular surface, the interior of the eye dropper may be contaminated with microorganisms, which gives rise to not a little risk of developing infectious eye diseases.

Patent Publication 1: JP-2006-282586-A
Patent Publication 2: JP-H10-324634-A
Patent Publication 3: JP-H07-166154-A
Patent Publication 4: JP-2010-106015-A
Patent Publication 5: JP-2008-88174-A
Non-patent Publication 1: Supervised by Yoshihisa Oguchi, Edited by Kazuo Tsubota, Ocular Surface *no Shindan to Chiryo* (Diagnosis and Treatment of Ocular Surface), Medical-Aoi Publications, Inc., pp83-87, 1993
Non-patent Publication 2: Charles H. Powell et al., Lipophilic versus hydrodynamic modes of uptake and release by contact lenses of active entities used in multipurpose solutions, Contact Lens & Anterior Eye, 33, 9-18, 2010
Non-patent Publication 3: Takashi Sakimoto, *Chiryo-you Kontakuto Renzu heno Boufuzai no Kyuchaku* (Adsorption of Preservatives on Therapeutic Soft Contact Lenses), Journal of Japan Contact Lens Society, 35, pp177-182, 1993
Non-patent Publication 4: Edited by Yuichi Ohashi, Ganka (Ophthalmology) New Insight 2, *Tengan-yaku-Joshiki to Hijoshiki* (Ophthalmic Solution—Common Sense and Preposterousness), Medical View Co., Ltd., pp36-43, 1994
Non-patent Publication 5: Yuichi Ohashi, Ganka (Ophthalmology) New Insight 2, *Tengan-yaku-Joshiki to Hijoshiki* (Ophthalmic Solution—Common Sense and Preposterousness), Medical View Co., Ltd., pp56-65, 1994

SUMMARY OF THE INVENTION

No effective ophthalmic solution has ever been obtained in which preservatives are inhibited from being adsorbed on soft contact lenses to improve safety on cornea, and of which preservative effect is sustained for safe use even if the ophthalmic solution is contaminated with microorganisms.

It is an object of the present invention to provide an ophthalmic solution of which preservative component, hexamethylene biguanide, contained therein is inhibited from being adsorbed on soft contact lenses and eye droppers.

The present inventors have made intensive researches for solving this problem, to develop an ophthalmic solution containing hydroxypropyl methylcellulose and a copolymer of a specific structure, to thereby complete the present invention.

According to the present invention, there is provided an ophthalmic solution comprising:

(A) hydroxypropyl methylcellulose having 28.0 to 30.0 mass % methoxy groups and 7.0 to 12.0 mass % hydroxypropoxy groups, both with respect to a total amount of said hydroxypropyl methylcellulose, at a methoxy group/hydroxypropoxy group ratio of 2.5 to 4.0 by mass, wherein a 2 mass % aqueous solution of said hydroxypropyl methylcellulose at 20° C. has a viscosity of 50 to 4000 mPa·s;

(B) sodium chloride or potassium chloride;

(C) hexamethylene biguanide represented by formula (1) or a salt thereof:

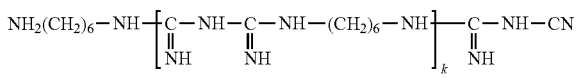

(1)

wherein k denotes the number of repeating units and is an integer of 3 to 40;

(D) 2-methacryloyloxyethyl phosphorylcholine/butyl methacrylate copolymer represented by formula (2):

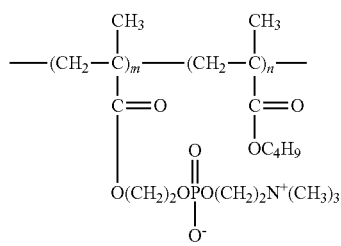

wherein m and n each denotes a molar ratio of respective constitutional unit, and m/n is 70/30 to 90/10 by mole; and
(E) water;
wherein a content of (A) is 0.1 to 0.2% w/v, a content of (B) is 0.01 to 1.5% w/v, a content of (C) is 0.00005 to 0.00015% w/v, and a content of (D) is 0.05 to 0.15% w/v, all with respect to a total amount of said ophthalmic solution.

According to another aspect of the present invention, there is provided a method for producing an ophthalmic solution comprising the steps of:

dispersing, in water heated to 70 to 90° C., (A) hydroxypropyl methylcellulose having 28.0 to 30.0 mass % methoxy groups and 7.0 to 12.0 mass % hydroxypropoxy groups, both with respect to a total amount of said hydroxypropyl methylcellulose, at a methoxy group/hydroxypropoxy group ratio of 2.5 to 4.0 by mass, to obtain a dispersion, wherein a 2 mass % aqueous solution of said hydroxypropyl methylcellulose at 20° C. has a viscosity of 50 to 4000 mPa·s;

cooling said dispersion down to 30 to 50° C.; and after said cooling, mixing, to said cooled dispersion, (B) sodium chloride or potassium chloride, (C) hexamethylene biguanide represented by formula (1) or a salt thereof:

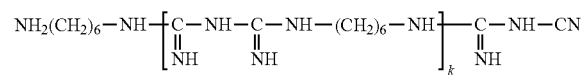

wherein k denotes the number of repeating units and is an integer of 3 to 40, and (D) 2-methacryloyloxyethyl phosphorylcholine/butyl methacrylate copolymer represented by formula (2):

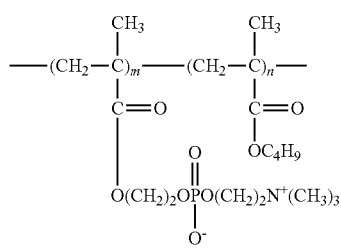

wherein m and n denote a molar ratio of respective constitutional units, and m/n is 70/30 to 90/10 by mole.

According to another aspect of the present invention, there is provided a method for inhibiting a preservative component in an ophthalmic solution from being adsorbed on a contact lens or an eye dropper, said method comprising preparing an ophthalmic solution to be brought into contact with a contact lens or an eye dropper by the steps comprising:

dispersing, in water heated to 70 to 90° C., (A) hydroxypropyl methylcellulose having 28.0 to 30.0 mass % methoxy groups and 7.0 to 12.0 mass % hydroxypropoxy groups, both with respect to a total amount of said hydroxypropyl methylcellulose, at a methoxy group/hydroxypropoxy group ratio of 2.5 to 4.0 by mass, to obtain a dispersion, wherein a 2 mass % aqueous solution of said hydroxypropyl methylcellulose at 20° C. has a viscosity of 50 to 4000 mPa·s;

cooling said dispersion down to 30 to 50° C.; and after said cooling, mixing, to said cooled dispersion, (B) sodium chloride or potassium chloride, (C) hexamethylene biguanide represented by formula (1) or a salt thereof:

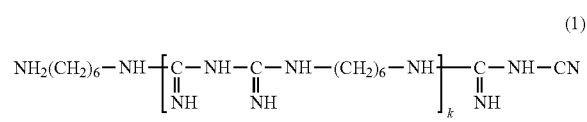

wherein k denotes the number of repeating units and is an integer of 3 to 40, and (D) 2-methacryloyloxyethyl phosphorylcholine/butyl methacrylate copolymer represented by formula (2):

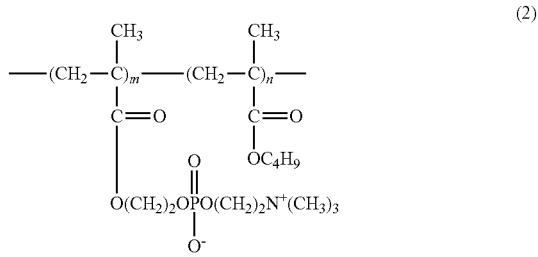

wherein m and n denote a molar ratio of respective constitutional units, and m/n is 70/30 to 90/10 by mole.

The ophthalmic solution according to the present invention, which has the particular composition containing hydroxypropyl methylcellulose and the copolymer, is capable of inhibiting hexamethylene biguanide, which is a preservative component contained in the ophthalmic solution, from being adsorbed on a soft contact lens or an eye dropper, so that the ophthalmic solution provides improved safety for cornea, and sustains the preservative effect which enables safe use of the ophthalmic solution even if contaminated with microorganisms.

The production method according to the present invention enables production of an ophthalmic solution which is capable of inhibiting hexamethylene biguanide from being adsorbed on a soft contact lens or an eye dropper, which has improved safety for cornea, and which sustains the preservative effect which enables safe use of the ophthalmic solution even if contaminated with microorganisms.

EMBODIMENTS OF THE INVENTION

The present invention will now be explained in detail.

The ophthalmic solution according to the present invention contains: (A) hydroxypropylmethylcellulose, (B) sodium chloride or potassium chloride; (C) hexamethylene biguanide represented by formula (1) or a salt thereof; (D) 2-methacryloyloxyethyl phosphorylcholine/butyl methacrylate copolymer represented by formula (2); and (E) water. Hereinbelow, above-defined (A) may sometimes be referred to as Component A, above-identified (B) as Component B, above-identified (C) as Component C, and above-identified (D) as Component D.

Component A in the ophthalmic solution of the present invention is hydroxypropyl methylcellulose having 28.0 to 30.0 mass % methoxy groups and 7.0 to 12.0 mass % hydroxypropoxy groups at a methoxy group/hydroxypropoxy group ratio of 2.5 to 4.0 by mass, and a 2 mass % aqueous solution of the hydroxypropyl methylcellulose at 20° C. has a viscosity of 50 to 4000 mPa·s. Preferably, the methoxy group/hydroxypropoxy group ratio is 3.0 to 3.6 by mass. At a mass ratio of less than 2.5 or over 4.0, the effect of inhibiting adsorption of the preservative, hexamethylene biguanide, on a soft contact lens or an eye dropper may be insufficient.

When the above-defined viscosity of hydroxypropyl methylcellulose is less than 50 mPa·s, the effect of inhibiting adsorption of the preservative on a soft contact lens may be insufficient, whereas when the above-defined viscosity of hydroxypropyl methylcellulose is over 4000 mPa·s, aseptic filterability, which is required in the production of an ophthalmic solution, may be poor, which may result in difficulties in producing an ophthalmic solution.

The content percentages of the methoxy groups and the hydroxypropoxy groups are average mass percentages of the methoxy groups and the hydroxypropoxy groups that have been introduced into cellulose, and may be calculated by a quantitative procedure described in, for example, the Japanese Pharmacopoeia or Japanese Pharmaceutical Excipients. According to the Japanese Pharmacopoeia, the content percentage may be calculated through measurement tests using the instruments and devices described in "(I) Instruments and apparatus" below, according to the quantitative procedure described in "(II) Procedure" below.

(I) Instruments and Apparatus

Reaction vial: A 5-mL pressure-tight serum vial, 20 mm in outside diameter, 50 mm in height, and 20 mm in outside diameter and 13 mm in inside diameter at the mouth, equipped with a septum having a fluororesin-faced butyl rubber and an air-tight seal using an aluminum crimp, or any system similar in structure.

Heater: A heating module with a square-shaped aluminum block having holes 20 mm in diameter and 32 mm in depth, so that the reaction vial fits. The heating module is also equipped with a magnetic stirrer capable of mixing the contents of the vial, or a reciprocal shaker that performs a reciprocating motion of 100 times/min can be used.

(II) Procedure

1) Into a serum vial, weigh about 65 mg of hydroxypropyl methylcellulose, add 0.06 to 0.10 g of adipic acid, 2.0 mL of internal standard solution, and 2.0 mL of hydriodic acid, immediately close the vial securely, and weigh the vial and contents.

2) Then, set the vial and contents in the square-shaped aluminum block, and mix the contents of the vial for about 1 hour using the magnetic stirrer or a reciprocal shaker, while heating the block so that the temperature of the contents is maintained at 130±2° C. If not with the magnetic stirrer or reciprocal shaker, shake the vial by hand at 5-minute intervals during the initial 30 minutes of the heating time.

3) Subsequently, allow the vial to cool to the room temperature, and weigh again. If the weight loss is not more than 0.50% of the contents or there is no evidence of a leak, use the upper layer of the mixture as a sample solution.

4) In a separate serum vial, weigh 0.06 to 0.10 g of adipic acid, 2.0 mL of internal standard solution, and 2.0 mL of hydriodic acid, and immediately close the vial securely. Weigh the vial and contents, add 45 µL of iodomethane and 15 to 22 µL of isopropyl iodide with a micro syringe through the septum, weigh again, and calculate the amount (mass) of the added components. Shake the vial well, and use the upper layer of the contents as a standard solution.

5) Analyze 1 to 2 µL of the sample solution and the standard solution thus obtained, by gas chromatographic measurement under the following conditions, and calculate the ratio $Q_{Ta}$, $Q_{Tb}$, $Q_{Sa}$, $Q_{Sb}$ of the peak area of each substance to that of the internal standard (n-octane from the internal standard solution).

<Conditions of Gas Chromatographic Measurement>

System: GC-2014 (SHIMADZU CORPORATION)

Detector: Thermal conductivity or hydrogen flame ionization

Column: 3- to 4-mm diameter x 1.8- to 3-m height glass column packed with 10% to 20% methyl silicone polymer for gas chromatography on 125 to 150 µm diatomaceous earth for gas chromatography, e.g., Silicone DC200 chromosorb W 20% 100/120 AW-DMCS (SHINWA CHEMICAL INDUSTRIES LTD.)

Column temperature: about 100° C.

Internal standard solution: o-xylene solution of n-octane (prepared so that n-octane is at 3% v/v)

Carrier gas: Helium for the thermal conductivity detector, and helium or nitrogen for the hydrogen flame ionization detector Carrier gas flow rate: Adjust so that the retention time of the internal standard is about 10 minutes.

From the ratios of the peak areas $Q_{Ta}$, $Q_{Tb}$, $Q_{Sa}$, $Q_{Sb}$ obtained from the above measurements, calculate the amounts of the methoxy groups (mass %) and the hydroxypropoxy groups (mass %) according to the formula:

$$\text{Amount of methoxy groups (mass \%)} = Q_{Ta}/Q_{Sa} \times M_{Sa}/M \times 21.86$$

$$\text{Amount of hydroxypropoxy groups (mass \%)} = Q_{Tb}/Q_{Sb} \times M_{Sb}/M \times 44.17$$

Here, the signs represent the following values:

$Q_{Ta}$: peak area corresponding to methoxy group in the sample solution/peak area of the internal standard $Q_{Sa}$: peak area of iodomethane in the standard solution/peak area of the internal standard $Q_{Tb}$: peak area corresponding to hydroxypropoxy group in the sample solution/peak area of the internal standard $Q_{Sb}$: peak area of isopropyl iodide in the standard solution / peak area of the internal standard $M_{Sa}$: amount of iodomethane taken (mg)

$M_{Sb}$: amount of isopropyl iodide taken (mg)

M: amount of hydroxypropyl methylcellulose taken, calculated on the dried basis (mg)

Sodium chloride or potassium chloride, as Component B in the ophthalmic solution according to the present invention, may be known products. Specifically, any products in conformity with the Japanese Pharmacopoeia may be used. Component B is sodium chloride or potassium chloride, or may contain both.

Component C in the ophthalmic solution according to the present invention is hexamethylene biguanide represented by formula (1):

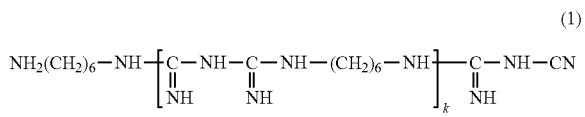

(1)

wherein k denotes the number of repeating units and is an integer of 3 to 40.

A salt of hexamethylene biguanide may be a hydrochloride, borate, acetate, gluconate, sulfonate, tartrate, or citrate. Commercial products, such as Cosmocil CQ (registered trademark, ARCH CHEMICALS) or BG-1 (SANYO CHEMICAL INDUSTRIES, LTD.) may be used.

The amount of hexamethylenebiguanide or a salt thereof is 0.00005 to 0.00015% w/v with respect to the total amount of the ophthalmic solution. At less than 0.00005% w/v, sufficient preservative effect for an ophthalmic solution may not be exhibited, whereas at over 0.00015% w/v, no improvement in the preservative effect may be expected.

Component D in the ophthalmic solution according to the present invention is a copolymer of 2-methacryloyloxyethyl phosphorylcholine (referred to as MPC hereinbelow) and butyl methacrylate, and represented by formula (2). The molar ratio of MPC and butyl methacrylate is 70:30 to 90:10.

The weight average molecular weight (Mw) of the copolymer is preferably 100000 to 1000000.

Component D has an effect of reducing cytotoxicity to be discussed later, but at a Mw of less than 100000, the effect of reducing cytotoxicity may be small. At a Mw of over 1000000, aseptic filterability, which is required in the production of an ophthalmic solution, may be poor.

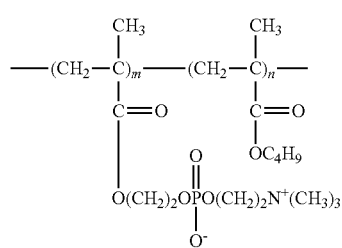

(2)

wherein m and n each denotes a molar ratio of respective constitutional unit, and m/n is 70/30 to 90/10 by mole.

Component D may be produced, for example, by the following process. Component D may be produced by polymerizing MPC and butyl methacrylate under deaerated conditions in the presence of a radical polymerization initiator, or in substitution with or in the atmosphere of an inert gas, such as nitrogen, argon, helium, or carbon dioxide gas, in a solvent, such as water, methanol, or ethanol, under heating or irradiation with light.

The ophthalmic solution according to the present invention is highly effective in inhibiting hexamethylene biguanide, which is a preservative contained in the ophthalmic solution, from being adsorbed on soft contact lenses, and improves safety on cornea. While soft contact lenses are categorized into five groups, i.e., Groups I to IV and silicone hydrogel lens, the ophthalmic solution according to the present invention is capable of significantly inhibiting hexamethylene biguanide from being adsorbed on silicone hydrogel lenses.

Next, a method for producing the ophthalmic solution according to the present invention is discussed.

The ophthalmic solution of the present invention is produced by dispersing Component A in hot water heated to 70 to 90° C., cooling the same down to 30 to 50° C. to obtain a solution, adding Components B, C, and D to the solution, and mixing the resulting mixture. Preferably, Components B to D are admixed in this order in the production. It is preferred that the cooled solution of Component A before Components B to D are added thereto, has a light transmittance at a wavelength of 500 nm of 90 to 100%, more preferably 95 to 100%, still more preferably 98 to 100%. By the production method discussed above, the light transmittance usually falls within the above-mentioned range. When the light transmittance is lower than 90%, Component A may not have been fully dissolved, so that it is preferred to prepare a cooled solution of Component A once again.

The heating and cooling in the production may be performed with any known instrument or apparatus as long as uniform heating and cooling of the entire solution is achieved. The dispersion may also be performed with any known instrument or apparatus as long as uniform dispersion of the dispersoid in the dispersion medium is achieved.

For uniform dispersion of Component A in water, it is preferred to heat the water to 70 to 90° C. and, for uniform dissolution of Component A, it is then preferred to cool the water to 30 to 50° C. after Component A is uniformly dispersed.

Incidentally, light transmittance (T) is a transmission (t) in percentage, which is, when monochromatic light is passed through a solution, a ratio of the intensity I of the transmitted light to the intensity $I_0$ of the incident light, and is expressed by the following formulae:

$$t=I/I_0$$

$$T=I/I_0 \times 100=100t$$

The light used in determining the light transmittance is monochromatic light having a wavelength of 500 nm.

The light transmittance T is expressed in 0 to 100% with no transmission of monochromatic light at 0% and full transmission of monochromatic light at 100%.

The light transmittance maybe determined, for example, with a ultraviolet-visible spectrophotometer V-550 (JASCO CORPORATION).

After the cooled solution of Component A is prepared, it is preferred to add Components B, C, and D in this order. It is sufficient that the order of addition of Components B, C, and D is in this order and, for example, components other than Components A to D may be added before the addition of Component B, between the addition of Components B and C, or between the addition of Components C and D.

The ophthalmic solution according to the present invention may optionally contain components discussed below, in addition to Components A to D.

For suppressing drying of the eyes and supplementing lacrymal fluid, a water-soluble polymer may be contained. The water-soluble polymer is not particularly limited as long as it is free of risk of eye irritation. For example, polyvinyl alcohol, polyvinylpyrrolidone, carboxyvinyl polymer, polyethylene glycol, hyaluronic acid or a salt thereof, chondroitin sulfate or a salt thereof, alginic acid or a salt thereof, carboxymethyl cellulose, hydroxyethyl cellulose, methylcellulose, a homopolymer of MPC, or a copolymer other than Component C using MPC.

Further, the following components may also be contained as long as the effects of the present invention are not impaired: surfactants, polyhydric alcohols, algefacients, chelating agents, inorganic salts, salts of organic acid, acids, bases, tonicity agents, antioxidants, or preservatives other than biguanides.

3. Light Transmittance of Ophthalmic Solution

The light transmittance of the ophthalmic solutions in Examples and Comparative Examples was determined according to The Japanese Pharmacopeia, Sixteenth Edition, "General Tests, Processes and Apparatus", "2.24 Ultraviolet-visible Spectrophotometry".

The details of Component A used, hydroxypropyl methylcellulose, is shown in Table 1.

TABLE 1

| Component | Product name | Methoxy group (mass %) | Hydroxypropoxy group (mass %) | Methoxy group/ hydroxypropoxy group (mass ratio) | Viscosity of 2% aqueous solution (mPa · s, @20° C.) |
|---|---|---|---|---|---|
| Hydroxypropyl methylcellulose (1) | METOLOSE (registered trademark) 60SH-50 | 29.1 | 8.2 | 3.5 | 50 |
| Hydroxypropyl methylcellulose (2) | METOLOSE (registered trademark) 60SH-4000 | 29.0 | 9.3 | 3.1 | 4000 |
| Hydroxypropyl methylcellulose (3) | METOLOSE (registered trademark) 65SH-400 | 28.0 | 6.0 | 4.7 | 400 |
| Hydroxypropyl methylcellulose (4) | METOLOSE (registered trademark) 90SH-100SR | 22.8 | 9.3 | 2.5 | 100 |

Note:
All manufactured by SHIN-ETSU CHEMICAL CO., LTD.

The surfactants may be, for example, higher fatty acids or salts thereof, alkylsulfuric acids or salts thereof, alkylsulfonic acids or salts thereof, polyoxyethylene alkylsulfuric acids or salts thereof, polyoxyethylene alkyl ethers, sugar esters, sugar ethers, sugar amides, imidazoline, or betaine. The polyhydric alcohols may be, for example, propylene glycol, glycerin, glucose, mannitol, sorbitol, xylitol, or trehalose. The algefacients may be, for example, menthol or camphor. The chelating agents may be, for example, ethylenediaminetetraacetic acid, citric acid, or etidronic acid. The inorganic salt may be, for example, borax, sodium hydrogen carbonate, sodium hydrogen phosphate, or sodium dihydrogen phosphate anhydrous. The salts of organic acid may be, for example, sodium citrate. The acids maybe, for example, boric, phosphoric, sulfuric, acetic, or hydrochloric acid. The bases maybe, for example, sodium hydroxide, potassium hydroxide, Trometamol, or monoethanolamine. Two or more of these components may be contained.

EXAMPLES

The present invention and its effect will now be explained in detail with reference to Examples and Comparative Examples, which do not limit the present invention.

1. pH of Ophthalmic Solution

The pH of the ophthalmic solutions in Examples and Comparative Examples was determined according to The Japanese Pharmacopeia, Sixteenth Edition, "General Tests, Processes and Apparatus", "2.54 pH Determination".

2. Osmotic Pressure of Ophthalmic Solution

The osmotic pressure of the ophthalmic solutions in Examples and Comparative Examples was determined according to The Japanese Pharmacopeia, Sixteenth Edition, "General Tests, Processes and Apparatus", "2.47 Osmolarity Determination". Specifically, the osmotic pressure was determined with an osmometer (Fiske Model 210 micro sample osmometer) by means of the freezing-point depression.

Example 1-1

To 80 g of purified water, (A) 0.1 g of hydroxypropyl methylcellulose (1) (METOLOSE (registered trademark) 60SH-50; 29.1% methoxy groups, 8.2% hydroxypropoxy groups, methoxy group/hydroxypropoxy group ratio of 3.5, viscosity of 2% aqueous solution at 20° C. of 50 mPa·s), (B) 0.63 g of sodium chloride, 0.1 g of potassium chloride, 0.4 g of boric acid, 0.0076 g of sodium hydroxide, (C) 0.0004 g of Cosmocil CQ (registered trademark) (20% aqueous solution, containing 0.00008 g of hexamethylene biguanide (weight average molecular weight of 2806, from which the number of the repeating units k in formula (1) is 14 in average)), and (D) 0.1 g of 2-methacryloyloxyethyl phosphorylcholine/butyl methacrylate copolymer (80 : 20) were added one after another, and stirred. Then, purified water was added to make the total volume to 100 mL. Then, the resulting mixture was subjected to filter sterilization to obtain a sterile ophthalmic solution. The osmotic pressure of this ophthalmic solution was 290 mOsm/kg, the pH was 7.4, and the appearance was colorless and transparent. The details are shown in Table 2.

Examples 1-2 to 1-10

A sterile ophthalmic solution was prepared in the same way as in Example 1-1, except that the components of the kinds and amounts shown in Table 2 were used. The appearance, pH, and the osmotic pressure of the obtained solution are shown in Table 2.

TABLE 2

|  |  |  | Example 1-1 | Example 1-2 | Example 1-3 | Example 1-4 | Example 1-5 |
|---|---|---|---|---|---|---|---|
| Amount (g) | Component A | Hydroxypropyl methylcellulose (1) | 0.1 |  | 0.1 | 0.1 |  |
|  |  | Hydroxypropyl methylcellulose (2) |  | 0.2 |  |  | 0.2 |
|  |  | Hydroxypropyl methylcellulose (3) |  |  |  |  |  |
|  |  | Hydroxypropyl methylcellulose (4) |  |  |  |  |  |
|  | Component B | Sodium chloride | 0.63 | 0.74 | 0.63 | 0.63 | 0.74 |
|  |  | Potassium chloride | 0.10 | 0.13 | 0.10 | 0.10 | 0.13 |
|  | Component C |  | 0.0004 (net: 0.00008) | 0.0004 (net: 0.00008) | 0.0004 (net: 0.00008) | 0.0004 (net: 0.00008) | 0.0004 (net: 0.00008) |
|  | Component D |  | 2.0 (net: 0.1) | 2.0 (net: 0.1) | 1.0 (net: 0.05) | 3.0 (net: 0.15) | 1.0 (net: 0.05) |
|  | Others | Boric acid | 0.4 |  | 0.4 | 0.4 |  |
|  |  | Borax |  |  |  |  |  |
|  |  | Disodium edetate dihydrate |  | 0.05 |  |  | 0.05 |
|  |  | Sodium hydrogenphosphate hydrate |  |  |  |  |  |
|  |  | Sodium dihydrogen phosphate anhydrous |  |  |  |  |  |
|  |  | Sodium hydroxide | 0.0076 | 0.0058 | 0.0076 | 0.0076 | 0.0058 |
|  |  | Purified water | Make total to 100 mL | Make total to 100 mL | Make total to 100 mL | Make total to 100 mL | Make total to 100 mL |
| Properties |  | Appearance | Colorless and transparent | Colorless and transparent | Colorless and transparent | Colorless and transparent | Colorless and transparent |
|  |  | pH | 7.4 | 7.2 | 7.4 | 7.4 | 7.2 |
|  |  | Osmotic pressure (mOsm/kg) | 290 | 278 | 288 | 289 | 281 |

|  |  |  | Example 1-6 | Example 1-7 | Example 1-8 | Example 1-9 | Example 1-10 |
|---|---|---|---|---|---|---|---|
| Amount (g) | Component A | Hydroxypropyl methylcellulose (1) |  | 0.1 |  |  | 0.1 |
|  |  | Hydroxypropyl methylcellulose (2) | 0.2 |  | 0.2 | 0.2 |  |
|  |  | Hydroxypropyl methylcellulose (3) |  |  |  |  |  |
|  |  | Hydroxypropyl methylcellulose (4) |  |  |  |  |  |
|  | Component B | Sodium chloride | 0.74 | 0.63 | 0.74 | 0.70 |  |
|  |  | Potassium chloride | 0.13 | 0.10 | 0.13 |  | 0.85 |
|  | Component C |  | 0.0004 (net: 0.00008) | 0.0004 (net: 0.00008) | 0.0004 (net: 0.00008) | 0.0004 (net: 0.00008) | 0.0004 (net: 0.00008) |
|  | Component D |  | 3.0 (net: 0.15) | 2.0 (net: 0.1) | 2.0 (net: 0.1) | 2.0 (net: 0.1) | 2.0 (net: 0.1) |
|  | Others | Boric acid |  |  |  | 0.4 | 0.4 |
|  |  | Borax |  |  |  |  |  |
|  |  | Disodium edetate dihydrate | 0.05 |  | 0.05 |  |  |
|  |  | Sodium hydrogenphosphate hydrate |  | 0.43 | 0.43 |  |  |
|  |  | Sodium dihydrogen phosphate anhydrous |  | 0.032 | 0.032 |  |  |
|  |  | Sodium hydroxide | 0.0058 |  |  | 0.0076 | 0.0076 |
|  |  | Purified water | Make total to 100 mL | Make total to 100 mL | Make total to 100 mL | Make total to 100 mL | Make total to 100 mL |
| Properties |  | Appearance | Colorless and transparent | Colorless and transparent | Colorless and transparent | Colorless and transparent | Colorless and transparent |
|  |  | pH | 7.2 | 7.4 | 7.2 | 7.4 | 7.4 |
|  |  | Osmotic pressure (mOsm/kg) | 279 | 287 | 278 | 287 | 276 |

Component C: Cosmocil CQ (registered trademark, ARCH CHEMICALS), 20% aqueous solution of hexamethylene biguanide hydrochloride
Component D: 2-methacryloyloxyethyl phosphorylcholine/butyl methacrylate copolymer solution, 5% aqueous solution (NOF CORPORATION)

Comparative Examples 1 to 7

A sterile ophthalmic solution was prepared in the same way as in Example 1-1, except that the components of the kinds and amounts shown in Table 3 were used. The appearance, pH, and the osmotic pressure of the obtained solution are shown in Table 3.

The specific test procedures are as follows:

1) A soft contact lens was placed in 1 mL of the ophthalmic solution of Example or Comparative Example in a contact lens case, soaked at 35° C. at 65% RH for over an hour, and then taken out.

TABLE 3

| | | | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Amount (g) | Component A | Hydroxypropyl methylcellulose (1) | | | 0.1 | 0.1 | 0.1 | 0.1 | |
| | | Hydroxypropyl methylcellulose (2) | | | | | | | 0.2 |
| | | Hydroxypropyl methylcellulose (3) | | 0.2 | | | | | |
| | | Hydroxypropyl methylcellulose (4) | 0.1 | | | | | | |
| | Component B | Sodium chloride | 0.63 | 0.74 | 0.63 | 0.63 | 0.63 | 0.005 | 1.0 |
| | | Potassium chloride | 0.1 | 0.13 | 0.1 | 0.1 | 0.1 | | 1.0 |
| | Component C | | 0.0004 (net: 0.00008) | 0.0004 (net: 0.00008) | 0.00015 (net: 0.00008) | 0.0004 (net: 0.00008) | 0.001 (net: 0.0002) | 0.0004 (net: 0.00008) | 0.0004 (net: 0.00008) |
| | Component D | | 2.0 (net: 0.1) | 2.0 (net: 0.1) | 1.0 (net: 0.05) | | 3.0 (net: 0.15) | 2.0 (net: 0.1) | 2.0 (net: 0.1) |
| | Others | Boric acid | 0.4 | | 0.4 | 0.4 | 0.4 | | |
| | | Borax | | | | | | | |
| | | Disodium edetate dihydrate | | 0.05 | | | | | 0.05 |
| | | Sodium hydrogenphosphate hydrate | | | | | | 6.1 | 0.43 |
| | | Sodium dihydrogen phosphate anhydrous | | | | | | 0.73 | 0.032 |
| | | Sodium hydroxide | 0.0076 | 0.0058 | 0.0076 | 0.0076 | 0.0076 | | |
| | | Purified water | Make total to 100 mL | Make total to 100 mL | Make total to 100 mL | Make total to 100 mL | Make total to 100 mL | Make total to 100 mL | Make total to 100 mL |
| Properties | | Appearance | Colorless and transparent | Colorless and transparent | Colorless and transparent | Colorless and transparent | Colorless and transparent | Colorless and transparent | Colorless and transparent |
| | | pH | 7.4 | 7.4 | 7.4 | 7.4 | 7.4 | 7.4 | 7.4 |
| | | Osmotic pressure (mOsm/kg) | 289 | 287 | 286 | 287 | 288 | 283 | 630 |

Component C: Cosmocil CQ (registered trademark, ARCH CHEMICALS), 20% aqueous solution of hexamethylene biguanide hydrochloride
Component D: 2-methacryloyloxyethyl phosphorylcholine/butyl methacrylate copolymer solution, 5% aqueous solution (NOF CORPORATION)

<Cytotoxicity Test on Soft Contact Lens Extract Using V79 Cells>

Soft contact lenses were cyclically soaked in the ophthalmic solution of Example or Comparative Example and in saline according to ISO 11981, to have the components of the ophthalmic solution of Example or Comparative Example absorbed on the soft contact lenses.

Then, according to ISO 10993-5 and Notification 0301 No. 20 issued by the Director of Office of Medical Devices Evaluation, Evaluation and Licensing Division, Pharmaceutical and Food Safety Bureau, Ministry of Health, Labor and Welfare, Japan, titled "Policy for Biological Safety Assessment Required for Application for Manufacturing and Marketing Approval of Medical Device", substances adsorbed on the soft contact lenses were extracted, and subjected to a cytotoxicity test (colony-forming assay) using Chinese hamster lung fibroblast cells (V79, JCRB0603).

The soft contact lenses used in the cytotoxicity test were 2-WEEK ACUVUE (registered trademark) (contact lens categories: Group IV) and ACUVUE OASYS (registered trademark) (contact lens categories: silicone hydrogel lens) (both JOHNSON & JOHNSON).

2) The soft contact lens taken out in 1) was placed in 1 mL of iso-saline in a separate contact lens case, and soaked for within an hour. The above operations, as one cycle, were repeated for 14 cycles.

3) Then, the soft contact lens was taken out of the contact lens case in 2), soaked in Eagle's minimum essential medium (MEM 10 medium) containing 10 vol % fetal bovine serum, and stored in a 5.0% $CO_2$ incubator at 37° C. for 24 hours to extract the substances adsorbed on the soft contact lens.

4) V79 cells were cultured on this extraction medium for 24 hours, fixed with methanol, and Giemsa-stained. The colonies of the V79 cells were counted, and the colony-forming ability was calculated.

5) In contrast to the V79 cells cultured on only a fresh medium as a control group, the group treated with the soft contact lens extract having a colony-forming ability of lower than that of the control group by over 30%, i.e., having a colony-forming ability of not higher than 70%, was evaluated as being cytotoxic.

The results of the cytotoxicity test on the soft contact lens extract using V79 cells are shown in Tables 4 and 5. Table 4 shows that the ophthalmic solutions of Examples 1-1 to 1-10 had low cytotoxicity, whereas Table 5 shows that the colony-forming abilities of the ophthalmic solutions of Comparative Examples 1 to 7 were not higher than 70%, which was evaluated as cytotoxic.

It was demonstrated in Examples 1-3 to 1-10 that the silicone hydrogen lens, ACUVUE OASYS (registered trademark), exhibited higher colony-forming ability and thus lower cytotoxicity. In Examples 1-1 and 1-2, little cytotoxicity and high safety was demonstrated.

tered trademark) 60SH-4000; 29.0% methoxy groups, 9.3% hydroxypropoxy groups, methoxy group/hydroxypropoxy group ratio of 3.1, viscosity of 2% aqueous solution at 20° C. of 4000 mPa·s) was introduced in small portions, and vigorously stirred with a magnetic stirrer for 30 minutes to obtain a dispersion. The light transmittance at 500 nm of this dispersion at 80° C. was 1.2%. This dispersion was cooled down to 50° C. to obtain a uniform solution. The light

TABLE 4

| | | Example 1-1 | Example 1-2 | Example 1-3 | Example 1-4 | Example 1-5 | Example 1-6 | Example 1-7 | Example 1-8 | Example 1-9 | Example 1-10 |
|---|---|---|---|---|---|---|---|---|---|---|---|
| Colony-forming ability | 2-WEEK ACUVUE (registered trademark) | 107% | 109% | 71% | 74% | 74% | 74% | 76% | 75% | 75% | 74% |
| | ACUVUE OASYS (registered trademark) | 121% | 101% | 85% | 86% | 89% | 87% | 89% | 85% | 88% | 85% |

TABLE 5

| | | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|
| Colony-forming ability | 2-WEEK ACUVUE (registered trademark) | 51% | 53% | 50% | 30% | 28% | 26% | 29% |
| | ACUVUE OASYS (registered trademark) | 49% | 52% | 47% | 29% | 35% | 27% | 31% |

Examples 2-1

To 80 g of purified water heated to 80° C., (A) 0.1 g of hydroxypropyl methylcellulose (1) was introduced in small portions, and vigorously stirred with a magnetic stirrer for 30 minutes to obtain a dispersion. The light transmittance at 500 nm of this dispersion at 80° C. was 53.0%. This dispersion was cooled down to 50° C. to obtain a uniform solution. The light transmittance at 500 nm of this solution at 50° C. was 99.4%. To this solution, (B) 0.63 g of sodium chloride, 0.1 g of potassium chloride, 0.4 g of boric acid, and 0.0076 g of sodium hydroxide, (C) 0.0004 g of Cosmocil CQ (registered trademark) (20% aqueous solution, containing 0.00008 g of hexamethylene biguanide), (D) 0.1 g of 2-methacryloyloxyethyl phosphorylcholine/butyl methacrylate copolymer (80 : 20) were added one after another, and stirred. The resulting solution, while maintained at 50° C., was stirred for 1 hour. Then, purified water was added to make the total volume to 100 mL. The light transmittance at 500 nm of the resulting solution at 30° C. was 100.0%. This solution was subjected to filter sterilization to obtain a sterile ophthalmic solution. The osmotic pressure of this ophthalmic solution was 290 mOsm/kg, the pH was 7.4, and the appearance was colorless and transparent. The details are shown in Table 6.

Example 2-2

To 80 g of purified water heated to 80° C., (A) 0.2 g of hydroxypropyl methylcellulose (2) (METOLOSE (registransmittance at 500 nm of this solution at 50° C. was 98.3%. To this solution, (B) 0.74 g of sodium chloride, 0.13 g of potassium chloride, and 0.0058 g of sodium hydroxide, 0.05 g of disodium edetate dihydrate, (C) 0.0004 g of Cosmocil CQ (registered trademark) (20% aqueous solution, containing 0.00008 g of hexamethylene biguanide), and (D) 0.1 g of 2-methacryloyloxyethyl phosphorylcholine/butyl methacrylate copolymer (80:20) were added one after another, and stirred. The resulting solution, while maintained at 50° C., was stirred for 1 hour. Then, purified water was added to make the total volume to 100 mL. The light transmittance at 500 nm of the resulting solution at 30° C. was 98.4%. This solution was subjected to filter sterilization to obtain a sterile ophthalmic solution. The osmotic pressure of this ophthalmic solution was 278 mOsm/kg, the pH was 7.2, and the appearance was colorless and transparent. The results are shown in Table 6.

The results of the cytotoxicity test on the soft contact lens extract using V79 cells with respect to the ophthalmic solutions of Examples 2-1 and 2-2 are shown in Table 7. Table 7 shows that the ophthalmic solutions of Examples 2-1 and 2-2 were demonstrated to have little cytotoxicity and high safety.

TABLE 6

| | | | Example 2-1 | Example 2-2 |
|---|---|---|---|---|
| Amount (g) | Component A | Hydroxypropyl methylcellulose (1) | 0.1 | |
| | | Hydroxypropyl | | 0.2 |

TABLE 6-continued

|  |  | Example 2-1 | Example 2-2 |
|---|---|---|---|
|  | methylcellulose (2) |  |  |
|  | Hydroxypropyl methylcellulose (3) |  |  |
|  | Hydroxypropyl methylcellulose (4) |  |  |
| Component B | Sodium chloride | 0.63 | 0.74 |
|  | Potassium chloride | 0.1 | 0.13 |
|  | Component C | 0.0004 (net: 0.00008) | 0.0004 (net: 0.00008) |
|  | Component D | 2.0 (net: 0.1) | 2.0 (net: 0.1) |
| Others | Boric acid | 0.4 |  |
|  | Borax |  |  |
|  | Disodium edetate dihydrate |  | 0.05 |
|  | Sodium hydrogenphosphate hydrate |  |  |
|  | Sodium dihydrogen phosphate anhydrous |  |  |
|  | Sodium hydroxide | 0.0076 | 0.0058 |
|  | Purified water | Make total to 100 mL | Make total to 100 mL |
| Properties | Light transmittance (@80° C.) | 53.0 | 1.2 |
|  | Light transmittance (@50° C.) | 99.4 | 98.3 |
|  | Light transmittance (ophthalmic solution, @30° C.) | 100.0 | 98.4 |
|  | Appearance | Colorless and transparent | Colorless and transparent |
|  | pH | 7.4 | 7.2 |
|  | Osmotic pressure (mOsm/kg) | 290 | 278 |

Component C: Cosmocil CQ (registered trademark, ARCH CHEMICALS), 20% aqueous solution of hexamethylene biguanide hydrochloride
Component D: 2-methacryloyloxyethyl phosphorylcholine/butyl methacrylate copolymer solution, 5% aqueous solution (NOF CORPORATION)

TABLE 7

|  |  | Example 2-1 | Example 2-2 |
|---|---|---|---|
| Colony-forming ability | 2-WEEK ACUVUE (registered trademark) | 108% | 108% |
|  | ACUVUE OASYS (registered trademark) | 123% | 104% |

<Storage Stability Test on Ophthalmic Solution>

A 15 mL polyethylene terephthalate eye dropper was charged with each ophthalmic solution prepared in Examples 1-1 to 1-10, 2-1, and 2-2, and the drug products of the present invention was stored in a depository at 40° C. at 75% RH according to the ICH Guidelines for 6 months. This storage is equivalent to three-year storage at room temperature. Hexamethylene biguanide in the charged solution was quantified at the beginning of the test and at the expiration of 6 months. The results of the storage stability test were evaluated such that, assuming that the percentage of the actual amount at the beginning of the test with respect to the indicated amount was 100% activity, the ophthalmic solution was determined to be compliant when the activity after the expiration of 6 months was within the range of 90 to 110% of the actual amount at the beginning of the test with respect to the indicated amount. The results of the storage stability test are shown in Tables 8 and 9.

TABLE 8

|  | At the beginning of test | At the expiration of 6 mths |
|---|---|---|
| Example 1-1 | 100% | 94% |
| Example 1-2 | 100% | 94% |
| Example 1-3 | 100% | 90% |
| Example 1-4 | 100% | 91% |
| Example 1-5 | 100% | 91% |
| Example 1-6 | 100% | 91% |
| Example 1-7 | 100% | 90% |
| Example 1-8 | 100% | 91% |
| Example 1-9 | 100% | 90% |
| Example 1-10 | 100% | 90% |

TABLE 9

|  | At the beginning of test | At the expiration of 6 mths |
|---|---|---|
| Example 2-1 | 100% | 99% |
| Example 2-2 | 100% | 99% |

The activity of hexamethylene biguanide at the expiration of 6 months was 90 to 94% in Examples 1-1 to 1-10, which was compliant. The activity at the expiration of 6 months was 99% (compliant) in both Examples 2-1 and 2-2, and accordingly little decrease of hexamethylene biguanide was observed, indicating significantly good storage stability.

What is claimed is:

1. An ophthalmic solution consisting of:
   (A) hydroxypropyl methylcellulose having 28.0 to 30.0 mass % methoxy groups and 7.0 to 12.0 mass % hydroxypropoxy groups, both with respect to a total amount of said hydroxypropyl methylcellulose, at a methoxy group/hydroxypropoxy group ratio of 2.5 to 4.0 by mass, wherein a 2 mass % aqueous solution of said hydroxypropyl methylcellulose at 20° C. has a viscosity of 50 to 4000 mPa·s;
   (B) sodium chloride or potassium chloride;
   (C) hexamethylene biguanide represented by formula (1) or a salt thereof:

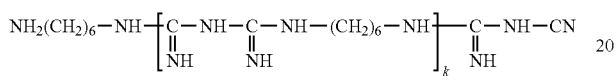

(1)

wherein k denotes the number of repeating units and is an integer of 3 to 40;
   (D) 2-methacryloyloxyethyl phosphorylcholine/butyl methacrylate copolymer represented by formula (2):

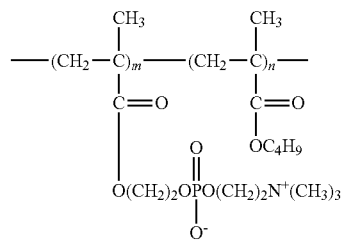

(2)

wherein m and n each denotes a molar ratio of respective constitutional unit, and m/n is 70/30 to 90/10 by mole; and
   (E) water; and
   optionally one or more components selected from the group consisting of boric acid, borax, disodium edetate dihydrate, sodium hydrogen phosphate hydrate, sodium dihydrogen phosphate anhydrous, and sodium hydroxide;
   wherein a content of (A) is 0.1 to 0.2% w/v, a content of (B) is 0.01 to 1.5% w/v, a content of (C) is 0.00005 to 0.00015% w/v, and a content of (D) is 0.05 to 0.15% w/v, all with respect to a total amount of said ophthalmic solution.

* * * * *